(12) United States Patent
Zeng et al.

(10) Patent No.: US 11,814,397 B2
(45) Date of Patent: Nov. 14, 2023

(54) METHODS FOR CRYSTALLIZATION OF DRUGS

(71) Applicant: BOSTON SCIENTIFIC SCIMED, INC., Maple Grove, MN (US)

(72) Inventors: Hongxia Zeng, Maple Grove, MN (US); Jonathan Pascal Chaky, Saint Paul, MN (US); Yen-Lane Chen, New Brighton, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 134 days.

(21) Appl. No.: 17/200,434

(22) Filed: Mar. 12, 2021

(65) Prior Publication Data
US 2021/0300938 A1   Sep. 30, 2021

Related U.S. Application Data

(60) Provisional application No. 63/000,861, filed on Mar. 27, 2020.

(51) Int. Cl.
*C07D 493/16* (2006.01)

(52) U.S. Cl.
CPC ........ *C07D 493/16* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 8,366,660 B2 | 2/2013 | Wang | |
| 8,377,499 B2 | 2/2013 | Kleiner et al. | |
| 8,403,910 B2 | 3/2013 | Wang | |
| 8,669,360 B2 | 3/2014 | Zeng et al. | |
| 9,056,152 B2 | 6/2015 | Kangas et al. | |
| 9,782,516 B2 | 10/2017 | Pacetti et al. | |
| 2008/0091008 A1 | 4/2008 | Viswanath et al. | |
| 2008/0118544 A1* | 5/2008 | Wang | A61L 29/16 424/448 |
| 2010/0285085 A1 | 11/2010 | Stankus et al. | |
| 2011/0144578 A1 | 6/2011 | Pacetti et al. | |
| 2011/0151104 A1 | 6/2011 | Kleiner et al. | |
| 2011/0160658 A1 | 6/2011 | Wang | |
| 2012/0321670 A1 | 12/2012 | Doshi et al. | |
| 2013/0035483 A1* | 2/2013 | Zeng | C07D 498/18 540/456 |
| 2014/0276360 A1 | 9/2014 | Pacetti et al. | |
| 2014/0277399 A1 | 9/2014 | Pacetti et al. | |
| 2016/0158228 A1* | 6/2016 | Nakagawa | A61K 9/0019 514/254.04 |
| 2020/0038559 A1 | 2/2020 | Zeng et al. | |

FOREIGN PATENT DOCUMENTS

WO   0033878 A2   6/2000

OTHER PUBLICATIONS

Chan et al; "Serendipitous Preparation of Crystals of Methotrexate and Attempts to Modify its Crystal Habit," Journal of Crystal Growth (94) pp. 488-498, North-Holland Amsterdam, 1989.
International Search Report and Written Opinion dated Jun. 9, 2021 for International Application No. PCT/US2021/022188.

* cited by examiner

*Primary Examiner* — Sudhakar Katakam
*Assistant Examiner* — Jennifer C Sawyer
(74) *Attorney, Agent, or Firm* — Seager, Tufte & Wickhem, LLP

(57) ABSTRACT

Methods are disclosed including methods for crystallizing a material such as a drug. An example method may include combining a nucleation initiator, a surfactant solution, and an amorphous form of a drug to form a drug precursor dispersion/suspension. The method may also include incubating the drug precursor dispersion/suspension to allow the drug to convert from the amorphous form to a crystalline form.

16 Claims, 2 Drawing Sheets

METHODS FOR CRYSTALLIZATION OF DRUGS

CROSS-REFERENCE TO RELATED APPLICATIONS

This application claims the benefit of priority under 35 U.S.C. § 119 to U.S. Provisional Application Ser. No. 63/000,861, filed Mar. 27, 2020, the entirety of which is incorporated herein by reference.

TECHNICAL FIELD

The present disclosure pertains to methods for crystallization, for example methods for crystallization of drugs.

BACKGROUND

A wide variety of medical devices have been developed for medical use, for example, intravascular use. Some of these devices include guidewires, catheters, balloons, stents, and the like. These devices are manufactured by any one of a variety of different manufacturing methods and may be used according to any one of a variety of methods. Some of these medical devices may include a drug, for example a crystalline form of a drug. Of the known medical devices and methods, each has certain advantages and disadvantages. There is an ongoing need to provide alternative medical devices as well as alternative methods for manufacturing and using medical devices. This may include the formation of crystalline materials (e.g., a crystalline form of a drug).

BRIEF SUMMARY

A method for crystallizing a drug is disclosed. The method comprises: combining a nucleation initiator, a surfactant solution, and an amorphous form of a drug to form a drug precursor dispersion/suspension; and incubating the drug precursor dispersion/suspension to allow the drug to convert from the amorphous form to a crystalline form.

Alternatively or additionally to any of the embodiments above, the drug includes everolimus.

Alternatively or additionally to any of the embodiments above, the nucleation initiator includes everolimus.

Alternatively or additionally to any of the embodiments above, the nucleation initiator includes everolimus microcrystals.

Alternatively or additionally to any of the embodiments above, the nucleation initiator, the surfactant solution, or both include a solvent.

Alternatively or additionally to any of the embodiments above, the solvent includes ethyl acetate, heptane, or both ethyl acetate and heptane.

Alternatively or additionally to any of the embodiments above, the solvent includes ethyl acetate and heptane and wherein the ratio of ethyl acetate to heptane is in the range of about 1:4 to 1:30.

Alternatively or additionally to any of the embodiments above, the solvent includes ethyl acetate and heptane and wherein the ratio of ethyl acetate to heptane is in the range of about 1:4 to 1:20.

Alternatively or additionally to any of the embodiments above, the solvent includes ethyl acetate and heptane and wherein the ratio of ethyl acetate to heptane is in the range of about 1:20.

Alternatively or additionally to any of the embodiments above, the surfactant solution includes polyoxyethylene (20) sorbitan monooleate.

Alternatively or additionally to any of the embodiments above, the surfactant solution includes polyoxyethylene (80) sorbitan monooleate.

Alternatively or additionally to any of the embodiments above, further comprising one or more of (a) filtering the crystalline form of the drug, (b) washing the crystalline form of the drug, and (c) drying the crystalline form of the drug.

Alternatively or additionally to any of the embodiments above, the crystalline drug material is substantially free of the surfactant.

Alternatively or additionally to any of the embodiments above, wherein incubating the drug precursor dispersion/suspension to allow the drug to convert from the amorphous form to a crystalline form occurs in the absence of agitating the drug precursor dispersion.

A method for converting amorphous everolimus to crystalline everolimus is disclosed. The method comprises: forming a drug precursor dispersion/suspension by combining a nucleation initiator, a surfactant solution, and an amorphous form of everolimus; wherein the drug precursor dispersion/suspension includes a solvent comprising ethyl acetate and heptane; wherein the surfactant solution includes polyoxyethylene sorbitan monooleate; and incubating the drug precursor dispersion/suspension to allow the amorphous form of everolimus to convert to everolimus microcrystals.

Alternatively or additionally to any of the embodiments above, the ratio of ethyl acetate to heptane in the solvent is in the range of about 1:4 to 1:20.

Alternatively or additionally to any of the embodiments above, the ratio of ethyl acetate to heptane in the solvent is about 1:20.

Alternatively or additionally to any of the embodiments above, the nucleation initiator includes everolimus.

Alternatively or additionally to any of the embodiments above, further comprising one or more of filtering everolimus microcrystals, washing the everolimus microcrystals, and drying the everolimus microcrystals that are substantially free of the surfactant.

A shelf-stable crystalline material is disclosed. The material comprises: everolimus microcrystals that are formed by crystallizing amorphous everolimus in the presence of a polyoxyethylene sorbitan monooleate surfactant; wherein the everolimus microcrystals are processed to be substantially free of the surfactant; and wherein the everolimus microcrystals have a width less than about 3 micrometers, a thickness less than about 1 micrometer, and a length less than about 10 micrometers.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
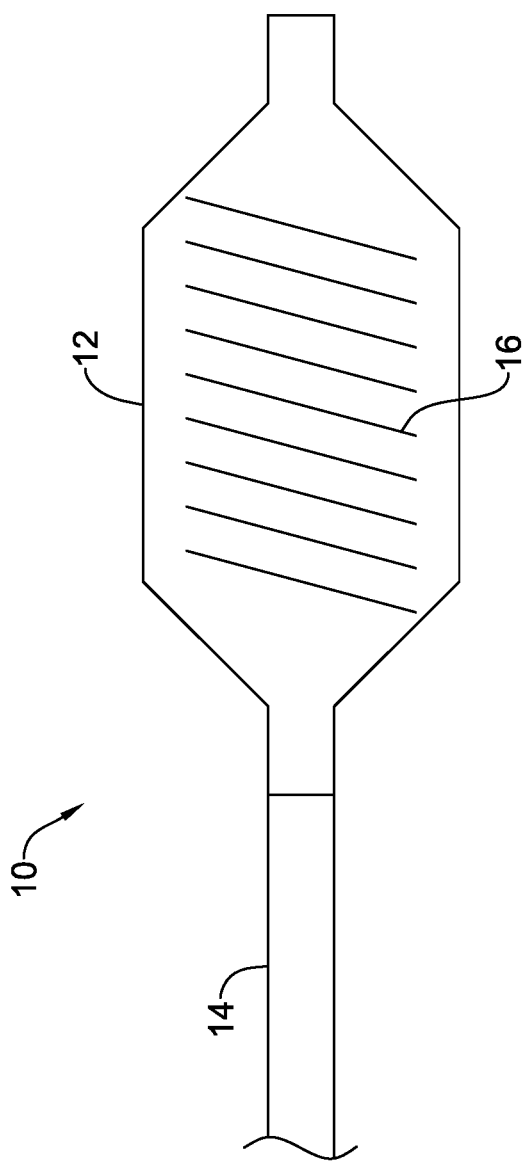
FIG. 1 is an example medical device.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Drug coated medical devices such as drug coated stents, drug coated balloons, and the like may be used to treat small vessel occlusions and/or vascular disease. Some example drugs that may be used with such devices includes paclitaxel, everolimus, etc. The application of the drug to the medical device may include applying a crystalline form of the drug to the surface of the medical devices. In at least some instances, the manufacturing process may include converting an amorphous form of the drug into a crystalline form. Disclosed herein are methods for converting an amorphous form of a material (e.g., a drug) into a crystalline form. In addition, disclosed herein are medical devices with such a coating applied thereto, methods for coating, etc.

Some example processes for converting an amorphous form of a drug into a crystalline form may generally include (a) preparing a suitable solvent, (b) preparing a nucleation initiator with the solvent, (c) combining/mixing the nucleation initiator with an amorphous form of a drug to form a drug precursor dispersion/suspension and (d) incubating the drug precursor dispersion/suspension to allow the amorphous form of the drug to convert to the crystalline form of the drug. The use of a suitable surfactant with the drug precursor dispersion/suspension may allow for the formation of drug crystals having a desirable morphology, allow for the formation of drug crystals having a desirable size and/or shape and/or aspect ratio, allow for the formation of coating suspensions with desirable stability, combinations thereof, and/or the like. Thus, at least some of the processes for converting an amorphous form of a drug into a crystalline form include (a) preparing a suitable solvent, (b) preparing a surfactant solution by combining/mixing the surfactant with the solvent, (c) preparing a nucleation initiator with the solvent, (d) combining/mixing the nucleation initiator with the surfactant solution and with an amorphous form of a drug to form a drug precursor dispersion/suspension and (e) incubating the drug precursor dispersion/suspension to allow the amorphous form of the drug to convert to the crystalline form of the drug.

In some embodiments, the drug may be a macrolide immunosuppressive (limus) drug. In some embodiments, the macrolide immunosuppressive drug is rapamycin, biolimus (biolimus A9), 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E, 4'S)-40-O-(4',5'-Dihydroxypent-2'-en-1'-yl)-rapamycin 40-O-(2-Hydroxy)ethoxycar-bonylmethyl-rapamycin, 40-O-(3-Hydroxy)propyl-rapamycin 40-O-(6-Hydroxy)hexyl-rapamycin 40-O-[2-(2-Hydroxy)ethoxy]ethyl-rapamycin 40-O-[(3S)-2,2-Dimethyldioxolan-3-yl]methyl-rapamycin, 40-O-[(2 S)-2,3-Dihydroxyprop-1-yl]-rapamycin, 40-O-(2-Acetoxy)ethyl-rapamycin 40-O-(2-Nicotinoyloxy)ethyl-rapamycin, 40-O-[2-(N-Morpholino)acetoxy]ethyl-rapamycin 40-O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 40-O-(2-Aminoethyl)-rapamycin, 40-O-(2-Acetaminoethyl)-rapamycin 40-O-(2-Nicotinamidoethyl)-rapamycin, 40-O-(2-(N-Methyl-imidazo-2'-ylcarbethoxamido)ethyl)-rapamycin, 40-O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), 42-[3-hydroxy-2-(hydroxymethyl)-2-methylpropanoate]rapamycin (temsirolimus), (42S)-42-Deoxy-42-(1H-tetrazol-1-yl)-rapamycin (zotarolimus), or derivative, isomer, racemate, diastereoisomer, prodrug, hydrate, ester, or analog thereof. Other drugs may include anti-inflammatory agents such as dexamethasone, prednisolone, corticosterone, budesonide, estrogen, sulfasalazine, mesalamine, and analogues thereof; antineoplastic/antiproliferative/anti-miotic agents such as paclitaxel, 5-fluorouracil, cisplatin, vinblastine, vincristine, epothilones, endostatin, angiostatin, thymidine kinase inhibitors, and analogues thereof; anesthetic agents such as lidocaine, bupivacaine, ropivacaine, and analogues thereof; anti-coagulants; and growth factors.

As indicated herein, example processes for converting an amorphous form of a drug into a crystalline form include preparing a suitable solvent. When the solvent is a singular material, preparing a suitable solvent may be as simple as placing the solvent in a suitable container. When the solvent is a mixture of materials, preparing a suitable solvent may include combining or mixing the solvents.

In at least some instances, the solvent may include alcohols such as methanol, ethanol (EtOH), isopropanol (IPA), n-butanol, isobutyl alcohol or t-butyl alcohol; acetonitrile (ACN); ethers such as tetrahydrofuran (THF) isopropyl ether (IPE), diethyl ether (DEE); ketone solvents such as acetone, 2-butanone (MEK), or methyl isobutyl ketone (MIBK); halogenated solvents such as dichloromethane (DCM), monofluorobenzene (MFB), α,α,α-trifluorotoluene (TFT), nitromethane (NM), ethyl trifluoroacetate (ETFA); aliphatic hydrocarbons such as hexane, heptane, or the like; aromatic hydrocarbons, such as toluene or xylenes; and ester solvents such as ethyl acetate. Mixed solvents such as ethyl acetate/heptane, acetone/water, IPA/water, IPA/THF, methanol/water, IPA/heptane, or THF/heptane can also be used, for example.

When mixtures of solvents are utilized, the mixture may have a suitable ratio of each material. For example, some example solvents may include a mixture of ethyl acetate and heptane. The ratio of ethyl acetate to heptane may be in the range of about 1:4 to 1:30, or about 1:4 to 1:20, or about 1:20. Other mixtures and/or ratios are contemplated. Thus, in some instances the process for converting an amorphous form of a drug into a crystalline form may include preparing a solvent, for example by mixing ethyl acetate with heptane.

The process for converting an amorphous form of a drug into a crystalline form may include preparing a surfactant solution (e.g., preparing a surfactant solution with the solvent). In at least some instances, the surfactant may include TWEEN 20™ (e.g., polysorbate 20, polyoxyethylene (20) sorbitan monooleate, or PEG (20) sorbitan monooleate), TWEEN 80™ (e.g., polysorbate 80, polyoxyethylene (80) sorbitan monooleate, or PEG (80) sorbitan monooleate), SPAN™ 80, SPAN™ 20, TRITON™ X-100, TRITON™ 400, a non-ionic surfactant, and/or the like. The surfactant solution may have a suitable concentration. For example, the concentration of the surfactant solution may be about 0.01-1% (by weight), about 0.05-0.5% (by weight), or about 0.1% (by weight).

The process for converting an amorphous form of a drug into a crystalline form may include preparing a nucleation initiator (e.g., preparing a nucleation initiator with the solvent). This process or step may also be termed "seeding". In at least some instances, the nucleation initiator may include a crystalline form of the drug suspended in a suitable solvent (e.g., which may or may not be the same solvent that is used to dissolve the amorphous form of the drug). When the drug utilized is everolimus, the nucleation initiator may include a suitable quantity of crystalline everolimus in a suitable solvent. The concentration of the of the crystalline everolimus in the solvent may be in the ration of about 0.1-10%, or about 0.1-2%, or about 0.5%. The crystalline everolimus may include everolimus microcrystals formed as described herein. Alternatively, the crystalline everolimus may include everolimus crystals having a different morphology.

The process for converting an amorphous form of a drug into a crystalline form may include mixing and/or combining the nucleation initiator with the surfactant solution and with an amorphous form of a drug to form a drug precursor dispersion/suspension. The amount of the amorphous form of the drug added may vary. For example, about 0.5-100 milligrams of everolimus may be added/dispersed per milliliter (e.g., per milliliter of solvent), or about 1-50 milligrams of everolimus may be added/dispersed per milliliter, or about 10-30 milligrams of everolimus may be added/dispersed per milliliter, or about 20 milligrams of everolimus may be dissolved per milliliter. In at least some instances, the drug dispersion solution may be termed and/or resemble a slurry.

The drug precursor dispersion/suspension may be incubated so that the amorphous form of the drug may converts to the crystalline form. In some instances, incubation may occur over a suitable time period on the order of a number of hours to a number of days. For example, incubation may occur over 24 hours. In some of these and in other instances, incubation may include a high-temperature or warm-temperature incubating step at a suitable temperature (e.g., at about 20° C. to 80° C., or at about 40° C. to 60° C., or at about 50° C.). In some instances, the high-temperature incubating may include agitating the drug precursor dispersion (e.g., using a suitable device such as an orbital shaker). However, in other instances, the high-temperature incubating step is free from agitating/agitation. The high-temperature incubating step may occur over a suitable time period on the order of a number of hours to a number of days. For example, incubation may occur over approximately two days. In some of these and in other instances, incubation may also include a low-temperature or cool-temperature incubating step at a suitable temperature (e.g., at about −10° C. to 10° C., or at about 0° C. to 5° C., or at about 4° C.). The low-temperature incubating step may occur over a suitable time period on the order of a number of hours to a number of days. For example, incubation may occur over several days.

In some instances, the process for converting an amorphous form of a drug into a crystalline form may include one or more of (a) filtering the crystalline form of the drug, (b) washing the crystalline form of the drug, and (c) drying the crystalline form of the drug. For example, some processes are contemplated that include filtering, washing, and drying the crystalline form of the drug. When doing so, the solvent, the surfactant, or both may be essentially completely removed from the drug crystals.

The crystalline form of the drug (e.g., the crystalline form of everolimus) formed by this process may result in crystals with a morphology, size, and shape that allow the formed crystals to be described as being microcrystals. In particular, the use of a surfactant in the crystallization process, along with a suitable solvent mixture, mixed at a suitable ratio, results in the formation of microcrystals. For the purposes of this disclosure, microcrystals may be understood to be crystals that could be described as relatively flat, thin sheets. Some example dimensions may include microcrystal having a width less than about 3 micrometers (e.g., having a non-zero width that is less than about 3 micrometers), a thickness less than about 1 micrometer (e.g., having a non-zero thickness that is less than about 1 micrometer), and a length less than about 10 micrometers (e.g., having a non-zero length that is less than about 10 micrometers). Microcrystals may be desirable for a number of reasons. For example, in some crystallization processes that form "larger", rod-like, or "non-micro" crystals, the resultant crystals can rapidly settle when suspended in a coating material/dispersion. This may make it more challenging to apply the drug crystals to a medical device. The microcrystals formed by the process described herein can be, for example, suspended in a coating material/dispersion and remain in suspension for an extended period of time (e.g., on the order of months or longer).

Figure 2:
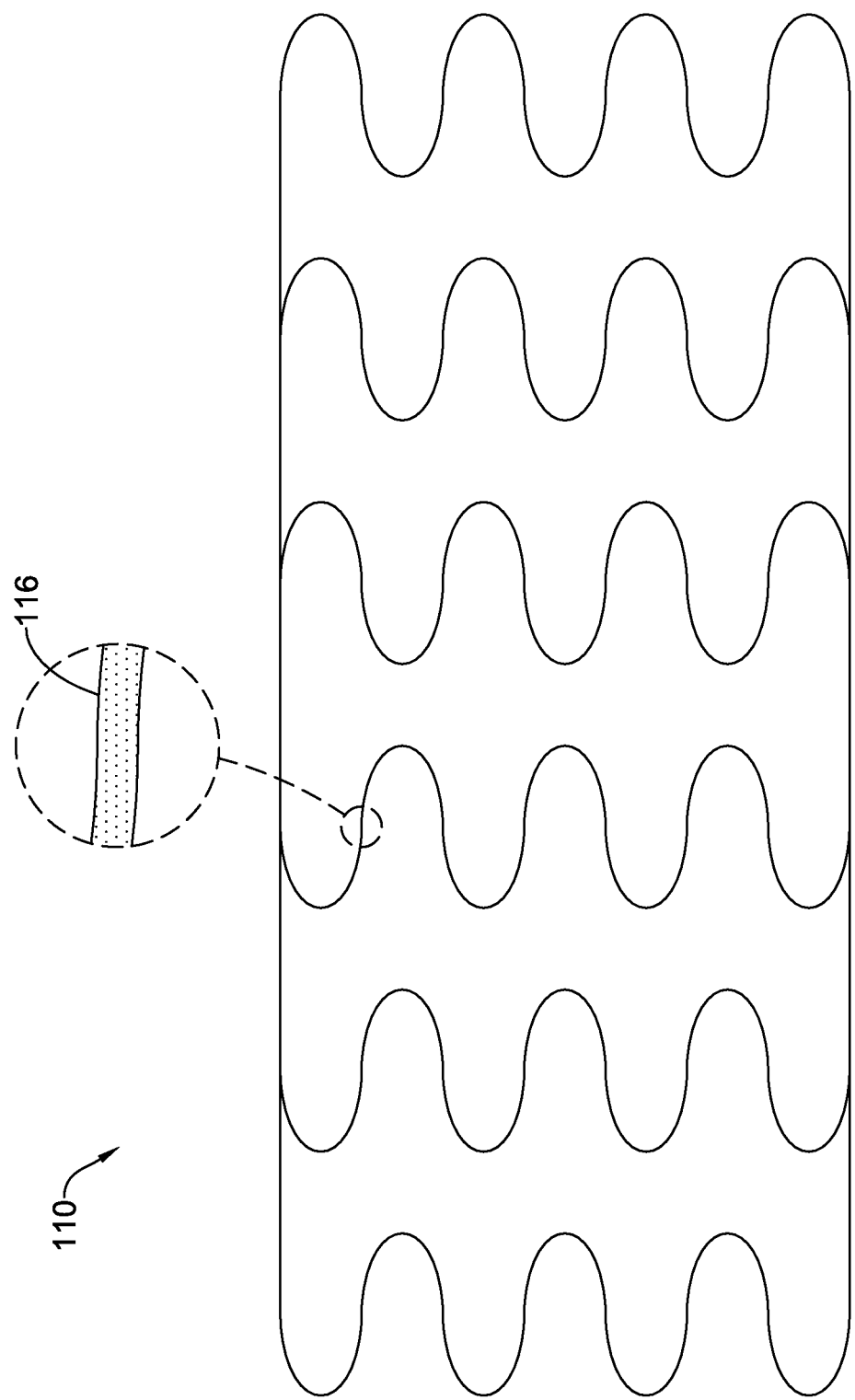
FIG. 2 is an example medical device.

In some instances, the microcrystals formed by the process disclosed herein may be suspend in a suitable coating material/dispersion. This may include the addition of a suitable excipient. An example excipient may include acetyl tri-butyl citrate (ATBC). In some instances, the drug microcrystals may be mixed with the excipient at a ratio of about 20:80 to about 90:10 or at a ratio of about 80:20. The coating material/dispersion may then be applied to a medical device using a suitable process. For example, the coating material/ dispersion may then be applied to a medical device by dip coating, roll coating, via a syringe, and/or the like. Some example drug coated medical devices, shown schematically, are shown in FIGS. 1-2. For example, FIG. 1 illustrates a drug coated balloon device 10 including a balloon 12 coupled to a catheter shaft 14. A drug coating 16 (e.g., crystalline everolimus including everolimus microcrystals formed as disclosed herein) may be disposed along the balloon 12. FIG. 2 illustrates a drug coated stent 110. A drug coating 116 (e.g., crystalline everolimus including everolimus microcrystals formed as disclosed herein) may be disposed along the stent 110.

EXAMPLES

The disclosure may be further clarified by reference to the following Examples, which serve to exemplify some embodiments, and not to limit the disclosure.

Example 1—Solvent Preparation

A solvent was prepared by mixing 200 mL of heptane with 10 mL of ethyl acetate in a bottle.

Example 2—Surfactant Solution Preparation

A surfactant solution was prepared by weighing 50 mg of TWEEN™ 80 into a container and adding 50 mL of the solvent prepared in Example 1 to the container. The surfactant solution was shaken/mixed until the surfactant (e.g., the TWEEN™ 80) was well dispersed within the solvent. Optionally the solution can be sonicated for 15 seconds. Furthermore, when reusing a previously made stock of surfactant solution, sonication may be utilized to re-disperse the surfactant (e.g., the TWEEN™ 80).

Example 3—Nucleation Initiator

A nucleation initiator was prepared by weighing 5 mg of everolimus microcrystals (e.g., from a previously run crystallization process) into a vial and adding 10 mL of the Solvent prepared in Example 1 to the vial.

Example 4—Crystallization 960 mg of amorphous everolimus was added to the vial containing the nucleation initiation prepared in Example 3.

30 mL of the surfactant solution prepared in Example 2 was added to the vial (e.g., the vial containing the nucleation initiator prepared in Example 3 and containing the 960 mg of amorphous everolimus).

The resultant combination of the nucleation initiation, the surfactant, and amorphous everolimus may be understood to be a drug precursor dispersion.

The drug precursor dispersion was sonicated while in the vial for 1 minute.

Crystallization was allowed to occur by incubating the vial (e.g., incubating the drug precursor dispersion) for 24 hours at room temperature.

After incubating, the vial may be sonicated for 1 minute.

The result of incubating the drug precursor dispersion is the formation of everolimus microcrystals (e.g., a microcrystal suspension).

The microcrystal suspension was filtered using a vacuum filtration system with a 0.45 micrometer polytetrafluoroethylene (PTFE) filter. This included transferring the microcrystal suspension to the filtration system, rinsing the vial with heptane to transfer any remaining crystals to the filter, pulling a vacuum on the filtration system, and rinsing the microcrystals three times with heptane.

The filter with the microcrystal was transferred to a clean, pre-weighed vial. The microcrystals were then allowed to dry in a vacuum chamber overnight.

The dried microcrystals were weighed and the percent yield was calculated.

The dried microcrystals were analyzed to determine the percent crystallinity via differential scanning calorimetry.

The dried microcrystals were placed in a freezer for long term storage.

The filtration process may include placing a drop of the microcrystal suspension on a disc for SEM analysis.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A method for crystallizing a drug, the method comprising:
    combining a nucleation initiator, a surfactant solution, and an amorphous form of a drug to form a drug precursor dispersion/suspension;
    wherein the nucleation initiator includes microcrystals characterized by a flat sheet morphology; and
    incubating the drug precursor dispersion/suspension to allow the drug to convert from the amorphous form to a crystalline form.

2. The method of claim 1, wherein the drug includes everolimus.

3. The method of claim 1, wherein the nucleation initiator includes everolimus.

4. The method of claim 1, wherein the nucleation initiator includes everolimus microcrystals.

5. The method of claim 1, wherein the nucleation initiator, the surfactant solution, or both include a solvent.

6. The method of claim 5, wherein the solvent includes ethyl acetate, heptane, or both ethyl acetate and heptane.

7. The method of claim 5, wherein the solvent includes ethyl acetate and heptane and wherein the ratio of ethyl acetate to heptane is in the range of about 1:4 to 1:30.

8. The method of claim 5, wherein the solvent includes ethyl acetate and heptane and wherein the ratio of ethyl acetate to heptane is in the range of about 1:4 to 1:20.

9. The method of claim 8, wherein the solvent includes ethyl acetate and heptane and wherein the ratio of ethyl acetate to heptane is in the range of about 1:20.

10. The method of claim 1, wherein the surfactant solution includes polyoxyethylene (20) sorbitan monooleate.

11. The method of claim 1, wherein the surfactant solution includes polyoxyethylene (80) sorbitan monooleate.

12. The method of claim 1, further comprising one or more of (a) filtering the crystalline form of the drug, (b) washing the crystalline form of the drug, and (c) drying the crystalline form of the drug.

13. The method of claim 12, wherein the crystalline drug material is substantially free of the surfactant.

14. The method of claim 1, wherein incubating the drug precursor dispersion/suspension to allow the drug to convert from the amorphous form to a crystalline form occurs in the absence of agitating the drug precursor dispersion.

15. A method for crystallizing a drug, the method comprising:
   combining a nucleation initiator, a surfactant solution, and an amorphous form of a drug to form a drug precursor dispersion/suspension;
   wherein the nucleation initiator includes everolimus microcrystals formed as relatively flat, thin sheets; and
   incubating the drug precursor dispersion/suspension to allow the drug to convert from the amorphous form to a crystalline form.

16. A method for crystallizing a drug, the method comprising:
   combining a nucleation initiator, a surfactant solution, and an amorphous form of a drug to form a drug precursor dispersion/suspension;
   wherein the nucleation initiator includes everolimus microcrystals having a non-zero width less than 3 micrometers and a non-zero thickness that is less than 1 micrometer; and
   incubating the drug precursor dispersion/suspension to allow the drug to convert from the amorphous form to a crystalline form.

\* \* \* \* \*